United States Patent [19]

Yonan

[11] 4,134,890

[45] Jan. 16, 1979

[54] 2-ARYL-2-[ω-(DIISOPROPYLAMINO)ALKYL]-ω-(AZABICYCLOALKYL)ALKANAMIDES

[75] Inventor: Peter K. Yonan, Morton Grove, Ill.

[73] Assignee: G. D. Searle & Co., Chicago, Ill.

[21] Appl. No.: 776,561

[22] Filed: Mar. 11, 1977

[51] Int. Cl.$^2$ ............... C07D 295/12; C07D 221/22; C07D 487/04; A61K 31/395
[52] U.S. Cl. ..................... 260/239 BA; 260/465 E; 544/349; 424/244; 424/250; 424/267; 546/112
[58] Field of Search ............... 260/239 BA, 293.54

[56] References Cited
U.S. PATENT DOCUMENTS

| | | | |
|---|---|---|---|
| 3,299,044 | 1/1967 | Cusic et al. | 260/239 BA |
| 3,586,713 | 6/1971 | Hoi et al. | 260/500.5 |

OTHER PUBLICATIONS

Steseth et al., J. Org. Chem. 34, 3007–3010 (1969).
Pala et al., J. Med. Chem. 16, 720–723 (1973).
Casadio et al. I, J. Med. Chem. 9, 707–714 (1966).
Casadio et al. II, J. Med. Chem. 8, 594–598 (1965).
Borovicka et al., Chem. Abs. 52, 5335i (1957).
Blicke et al., J. Amer. Chem. Soc. 75, 4334–4335 (1953).
Instituto de Angeli, Derwent 14,754 of Dutch Patent 6,405,327, pub. 11-16-1964.

*Primary Examiner*—Mark L. Berch
*Attorney, Agent, or Firm*—Dragan J. Karadzic

[57] ABSTRACT

Novel 2-aryl-2-[ω-(diisopropylamino)alkyl]-ω-(azabicycloalkyl)alkanamides are described herein. The present compounds are useful as anti-arrhythmic agents. The compounds are prepared by reacting an appropriate disubstituted acetonitrile with an appropriate ω-(azabicycloalkyl)alkyl halide and subsequent hydrolysis of the resulting nitrile with concentrated sulfuric acid.

7 Claims, No Drawings

2-ARYL-2-[ω-(DIISOPROPYLAMINO)ALKYL]-ω-(AZABICYCLOALKYL)ALKANAMIDES

The present invention relates to 2-aryl-2-[ω-(diisopropylamino)alkyl]-ω-(azabicycloalkyl)alkanamides having the following general formula

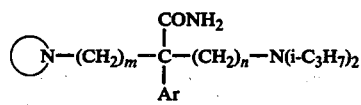

wherein Ar is phenyl, trifluoromethylphenyl, or phenyl substituted with 1 or 2 halogen or lower alkyl having from 1 to 4 carbon atoms;

represents an azabicyclic ring having from 6 to 9 carbon atoms which may contain further hetero atom; and m and n are each integers from 2 to 4 inclusive.

The halogens comprehended as substituent in the phenyl are fluorine, chlorine, bromine and iodine, with fluorine and chlorine being preferred.

The lower alkyls comprehended as substituents in the phenyl are methyl, ethyl, propyl, butyl and the branched-chain isomers thereof, with methyl being preferred.

The positioning of these halogens and lower alkyls relative to the point of attachment of the phenyl or, where two are present, to each other is not critical. Thus, within the scope of this invention are o-, m-, and p-monosubstituted phenyls of the type described above such as o-chlorophenyl, m-fluorophenyl and p-tolyl; and 2,3-, 2,4-, 2,5-, 2,6-, 3,4-, and 3,5-disubstituted phenyls of the type described above such as 2,3-dichlorophenyl, 2,4-difluorophenyl, 2-chloro-5-fluorophenyl, 2-fluoro-6-methylphenyl, 3,4-dimethylphenyl, and 3-chloro-4-methylphenyl.

The azabicyclic rings contemplated in the above formula are exemplified by 3-azabicyclo[3.2.2]nonane, 2-azabicyclo[2.2.2]octane.

The example of azabicyclic ring containing further hetero atom is pyrrolo[1,2-a]pyrazine.

Equivalent to the free bases of formula (I) for the purposes of this invention are non-toxic acid addition salts thereof having the formula

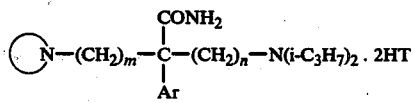

wherein

Ar, m and n are as previously defined; and T represents 1 equivalent of an anion — for example, fluoride, bromide, iodide, nitrate, phosphate, sulfate, sulfamate, methyl sulfate, ethyl sulfate, benzenesulfonate, toluenesulfonate, acetate, lactate, succinate, maleate, tartrate, citrate gluconate, ascorbate benzoate, cinnamate, or the like — which, in combination with the cationic portion of a salt aforesaid, is neither biologically nor otherwise incompatible.

Embodiments of the present invention having the formula

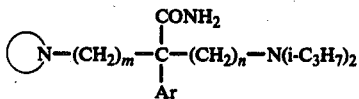

wherein

is 3-azabicyclo[3.2.2]non-3-yl, 2-azabicyclo[2.2.2]oct-2-yl or pyrrolo[1,2-a]pyrazin-2-yl; Ar is phenyl or phenyl substituted with 1 or 2 halogen; and m and n are each integers from 2 to 4 inclusive are preferred.

Other preferred embodiments are compounds having the formula

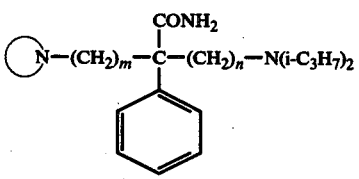

wherein

is 3-azabicyclo[3.2.2]non-3-yl, 2-azabicyclo[2.2.2]oct-2-yl or pyrrolo[1,2-a]pyrazin-2-yl, and m and n are each integers from 2 to 4 inclusive and of these embodiments compounds in which m and n each equal 2 are particularly preferred.

Compounds of this invention having the formula

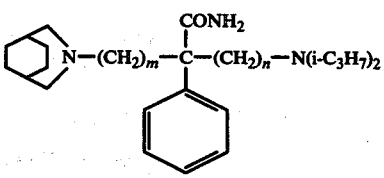

wherein m and n are each integers from 2 to 4 inclusive are particularly preferred embodiments.

The compounds of this invention are useful because of their pharmaceutical properties. In particular, they possess activity of anti-arrhythmic agents. Thus, they bring about a return to normal heart rhythm in animals in which the heart rhythm has been irregular.

The anti-arrhythmic activity of the present compounds has been demonstrated in the following way. Ventricular arrhythmia is induced by a 2-stage ligation of the anterior descending branch of the left coronary artery in each of two or more dogs. Quantities of a test compound (5mg/kg) are administered intravenously at intervals to a possible maximum accumulated dose of 15 mg/kg. A compound is rated active if it produces at least 25% reduction in ectopic beats for a period of at least 10 minutes in half or more of the dogs tested. Among the compounds of this invention which have been found particularly active in this test is the representative compound 2-[2-(diisopropylamino)ethyl]-2-phenyl-4-(3-azabicyclo[3.2.2]non-3-yl)butyramide.

The compounds of this invention are conveniently prepared by reacting disubstituted acetonitrile of the formula

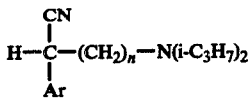

wherein Ar and n are as previously defined, with a haloalkyl amine of the formula

wherein

and m are as previously defined and halogen is preferably chlorine, in the presence of a strong base such as sodium amide in an inert solvent such as toluene with heating and subsequently hydrolyzing the resulting nitrile of the formula

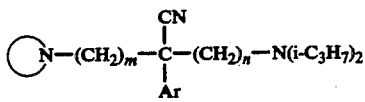

wherein

Ar, m and n are as previously defined; with concentrated sulfuric acid.

The invention will appear more fully from the examples which follow. These examples are given by way of illustration only and are not to be construed as limiting the invention either in spirit or in scope as many modifications both in materials and in methods will be apparent from this disclosure to those skilled in the art. In these examples, temperatures are given in degrees Centigrade (° C.) and quantities of materials in parts by weight, unless parts by volume is specified. The relationship between parts by weight and parts by volume is the same as that existing between grams and milliliters.

EXAMPLE 1

To a solution of 58 parts of α-phenylacetonitrile in 300 parts by volume of toluene is added 83 parts of 2-chloro-N,N-diisopropylethylamine dissolved in 300 parts by volume of toluene. The mixture is heated with stirring to about 80° C. and then 22 parts of sodium amide is added slowly over a period of 30 minutes. The mixture is heated at 80° C. for another 30 minutes and then cooled to room temperature. 500 Parts by volume of water is then added to the mixture and the organic layer is separated and extracted with dilute hydrochloric acid. The aqueous acidic extract is made alkaline by the addition of dilute sodium hydroxide. The alkaline mixture is extracted with ether and the ether extract dried over calcium sulfate, concentrated and distilled to afford α-[2-(diisopropylamino)ethyl]-α-phenylacetonitrile, as an oil. This compound is represented by the following structural formula

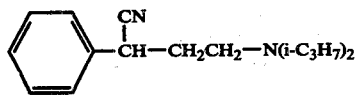

Substitution of the appropriate acetonitrile in the procedure detailed above affords the following compounds: α-(p-chlorophenyl)-α-[2-(diisopropylamino)ethyl]acetonitrile; α-(o-fluorophenyl)-α-[2-(diisopropylamino)ethyl]acetonitrile; α-(3,4-difluorophenyl)-α-[2-(diisopropylamino)ethyl]acetonitrile; α-[2-(diisopropylamino)ethyl]-α-(p-tolyl)acetonitrile; and α-[2-(diisopropylamino)ethyl]-α-(o-trifluoromethylphenyl)acetonitrile.

EXAMPLE 2

A solution of 16 parts of α-[2-(diisopropylamino)ethyl]-α-phenylacetonitrile and 5 parts of sodium amide in 200 parts by volume of toluene is heated to about 100° C. over a period of 15 minutes and then 20 parts of 3-(2-chloroethyl)-3-azabicyclo[3.2.2]nonane in 100 parts by volume of toluene is added slowly over a period of 20 minutes. This mixture is heated at 105°-110° C. for an hour and then cooled to room temperature when 200 parts by volume of water is added. The organic layer is separated, dried over calcium sulfate, concentrated, and then distilled to afford 2-[2-(diisopropylamino)ethyl]-2-phenyl-4-(3-azabicyclo[3.2.2]non-3-yl)butyronitrile, as an oil. This compound is represented by the following structural formula

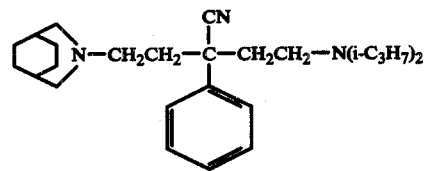

Substitution of the appropriate disubstituted acetonitrile in the above detailed procedure affords the following butyronitriles:

2-(p-chlorophenyl)-2-[2-(diisopropylamino)ethyl]-4-(3-azabicyclo[3.2.2]non-3-yl)butyronitrile;

2-(o-fluorophenyl)-2-[2-(diisopropylamino)ethyl]-4-(3-azabicyclo[3.2.2]non-3-yl)butyronitrile;

2-(3,4-difluorophenyl)-2-[2-(diisopropylamino)ethyl]-4-(3-azabicyclo[3.2.2]non-3-yl)butyronitrile;

2-[2-(diisopropylamino)ethyl]-2-(p-tolyl)-4-(3-azabicyclo[3.2.2]non-3-yl)butyronitrile; and 2-[2-(diisopropylamino)ethyl]-2-(o-trifluoromethylphenyl)-4-(3-azabicyclo[3.2.2]non-3-yl)butyronitrile.

EXAMPLE 3

5 Parts of 2-[2-(diisopropylamino)ethyl]-2-phenyl-4-(3-azabicyclo[3.2.2]non-3-yl)butyronitrile is dissolved in 50 parts by volume of concentrated sulfuric acid and the resulting solution is cooled to about 0° C. and then made alkaline by the addition of dilute sodium hydroxide. The alkaline solution is extracted with ether, the ether extract dried over calcium sulfate and stripped of solvent to afford, after crystallization from pentane, 2-[2-(diisopropylamino)ethyl]-2-phenyl-4-(3-azabicyclo[3.2.2]non-3-yl)butyramide. This compound is represented by the following structural formula

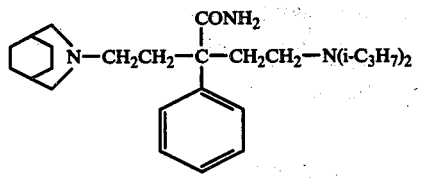

Substitution of the appropriate butyronitrile in the procedure detailed above affords the following compounds:

2-(p-chlorophenyl)-2-[2-(diisopropylamino)ethyl]-4-(3-azabicyclo[3.2.2]non-3-yl)butyramide;

2-(o-chlorophenyl)-2-[2-(diisopropylamino)ethyl]-4-(3-azabicyclo[3.2.2]non-3-yl)butyramide;

2-(3,4-difluorophenyl)-2-[2-(diisopropylamino)ethyl]-4-(3-azabicyclo[3.2.2]non-3-yl)butyramide;

2-[2-(diisopropylamino)ethyl]-2-(p-tolyl)-4-(3-azabicyclo[3.2.2]non-3-yl)butyramide; and 2-[2-(diisopropylamino)ethyl]-2-(o-trifluoromethylphenyl)-4-(3-azabicyclo[3.2.2]non-3-yl)butyramide.

EXAMPLE 4

Substitution of an equivalent quantity of 2-(2-chloroethyl)pyrrolo[1,2-a]pyrazine for 3-(2-chloroethyl)-3-azabicyclo[3.2.2]nonane called for in Example 2 affords, by the procedure detailed in that example, 2-[2-(diisopropylamino)ethyl]-2-phenyl-4-(pyrrolo[1,2-a]pyrazin-2-yl)butyronitrile, as an oil.

When an equivalent quantity of the above butyronitrile is substituted in the procedure of Example 3, there is obtained after crystallization from a mixture of methylene chloride and hexane, 2-[2-(diisopropylamino)ethyl]-2-phenyl-4-(pyrrolo[1,2-a]pyrazin-2-yl)butyramide. This compound is represented by the following structural formula

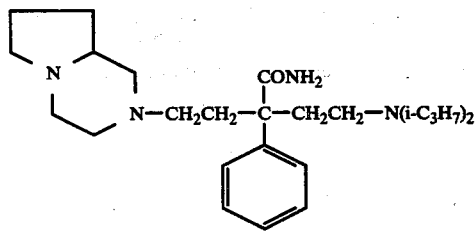

EXAMPLE 5

Substitution of an equivalent quantity of 3-(3-chloropropyl)-3-azabicyclo[3.2.2]nonane for 3-(2-chloroethyl)-3-azabicyclo[3.2.2]nonane called for in Example 2 and substantial repetition of the procedure detailed in that example affords 2-[2-(diisopropylamino)ethyl]-2-phenyl-5-(3-azabicyclo[3.2.2]non-3-yl)valeronitrile, as an oil.

When an equivalent quantity of the above valeronitrile is substituted in the procedure of Example 3, there is obtained, after crystallization from hexane, 2-[2-(diisopropylamino)ethyl]-2-phenyl-5-(3-azabicyclo[3.2.2]non-3-yl)valeramide. This compound is represented by the following formula

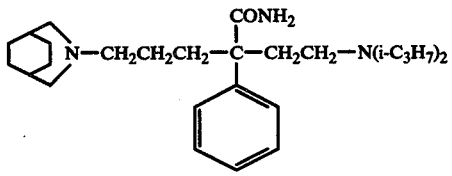

EXAMPLE 6

Substitution of an equivalent quantity of 2-(2-chloroethyl)-2-azabicyclo[2.2.2]octane for 3-(2-chloroethyl)-3-azabicyclo[3.2.2]nonane called for in Example 2 and substantial repetition of the procedure there detailed affords 2-[2-(diisopropylamino)ethyl]-2-phenyl-4-(2-azabicyclo[2.2.2]oct-2-yl)butyronitrile, as an oil.

When an equivalent quantity of the above butyronitrile is substituted in the procedure of Example 3, there is obtained, after crystallization from a mixture of methylene chloride and hexane, 2-[2-(diisopropylamino)ethyl]-2-phenyl-4-(2-azabicyclo[2.2.2]oct-2-yl)butyramide. This compound is represented by the following structural formula

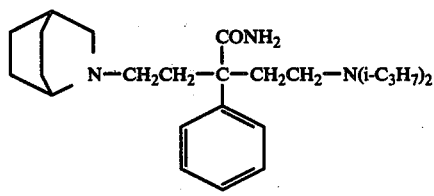

EXAMPLE 7

To a solution of 10 parts of 2-[2-(diisopropylamino)ethyl]-2-phenyl-4-(3-azabicyclo[3.2.2]non-3-yl)butyramide in 350 parts by volume of ether is added dropwise with stirring 2 molar equivalents of hydrochloric acid in isopropyl alcohol. The mixture is stirred for about 2 hours when the resulting salt is separated by filtration to afford 2-[2-(diisopropylamino)ethyl]-2-phenyl-4-(3-azabicyclo[3.2.2]non-3-yl)butyramide dihydrochloride.

EXAMPLE 8

A mixture of 6 parts of 2-[2-(diisopropylamino)ethyl]-2-phenyl-4-(3-azabicyclo[3.2.2]non-3-yl)butyramide, 20 parts by volume of methyl iodide and 150 parts by volume of acetone is heated in a bomb at 65° C. for about 3 hours. To the solidified reaction mixture is then added additional quantity of acetone and the solid is separated by filtration. The solid which is crystallized from a mixture of ethyl alcohol and ether is 2-[2-(diisopropylamino)ethyl]-2-phenyl-4-(3-azabicyclo[3.2.2]-non-3-yl)butyramide bismethiodide. This compound is represented by the following structural formula

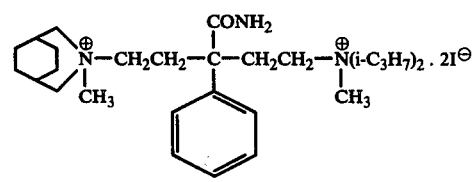

EXAMPLE 9

Substitution of an equivalent quantity of 3-chloro-N,N-diisopropylpropylamine for 2-chloro-N,N-diisopropylethylamine called for in Example 1 affords, by the procedure detailed in that example, α-[3-(diisopropylamino)propyl]-α-phenylacetonitrile.

Substitution of the above acetonitrile in the procedure of Example 6 and substantial repetition of the procedure detailed in that example affords 2-[3-(diisopropylamino)propyl]-2-phenyl-4-(2-azabicyclo[2.2.2]oct-2-yl)butyramide.

EXAMPLE 10

To a solution of 20 parts of α-phenylacetonitrile in 300 parts by volume of toluene is added 94 parts of 3-(2-chloroethyl)-3-azabicyclo[3.2.2]nonane dissolved in 500 parts by volume of toluene. The mixture is heated with stirring to about 80° C. and then 17 parts of sodium amide is added slowly over a period of 30 minutes. The mixture is heated at 80° C. for another 30 minutes and then cooled to room temperature. 500 Parts by volume of water is then added to the mixture and the organic layer separated and extracted with dilute hydrochloric acid. The aqueous acidic extract is made alkaline by the addition of dilute sodium hydroxide. The alkaline mixture is extracted with ether, the ether extract dried over calcium sulfate and distilled to afford 2-phenyl-4-(3-azabicyclo[3.2.2]non-3-yl)butyronitrile.

Successive repetition of the procedure described in Examples 2 and 3 using the above butyronitrile as the starting material affords, after crystallization from isopropyl alcohol, α, α-bis[2-(3-azabicyclo[3.2.2]non-3-yl)ethyl]-α-phenylacetamide. This compound is represented by the following structural formula

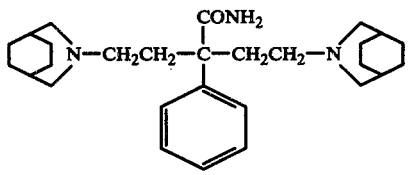

What is claimed is:

1. A compound having the formula

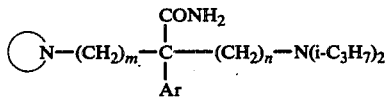

and the non-toxic pharmacologically acceptable acid addition salts thereof; where

is 3-azabicyclo[3.2.2]non-3-yl, or 2-azabicyclo[2.2.2]oct-2-yl,[or pyrrolo[1,2-a]pyrazin-2-yl;] Ar is phenyl or phenyl substituted with 1 or 2 halogen; and m and n are each integers from 2 to 4 inclusive.

2. A compound according to claim 1 which is 2-[2-(diisopropylamino)ethyl]-2-phenyl-4-(2-azabicyclo[2.2.2]oct-2-yl)butyramide.

3. A compound according to claim 1 which is 2-[2-(diisopropylamino)ethyl]-2-phenyl-[4]5-(3-azabicyclo[3.2.2]non-3-yl)valeramide.

4. A compound according to claim 1 having the formula

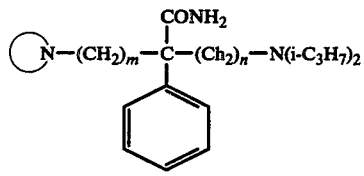

and the non-toxic pharmacologically acceptable acid addition salts thereof; where

is 3-azabicyclo[3.2.2]non-3-yl, or 2-azabicyclo[2.2.2]oct-2-yl,[or pyrrolo[1,2-a]pyrazine-2-yl;] and m and n are each integers from 2 to 4 inclusive.

5. A compound according to claim 1 having the formula

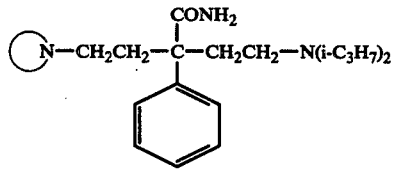

and the non-toxic pharmacologically acceptable acid addition salts thereof; where

is 3-azabicyclo[3.2.2]non-3-yl, or 2-azabicyclo[2.2.2]oct-2-yl[or pyrrolo[1,2-a]pyrazin-2-yl].

6. A compound according to claim 1 having the formula

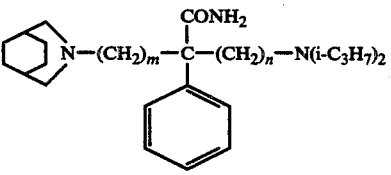

and the non-toxic pharmacologically acceptable acid addition salts thereof; wherein m and n are each integers from 2 to 4 inclusive.

7. A compound according to claim 1 which is 2-[2-(diisopropylamino)ethyl]-2-phenyl-4-(3-azabicyclo[3.2.2]non-3-yl)butyramide.